(12) United States Patent
Gardner et al.

(10) Patent No.: US 6,506,695 B2
(45) Date of Patent: Jan. 14, 2003

(54) BREATHABLE COMPOSITE AND METHOD THEREFOR

(75) Inventors: Hugh C. Gardner, Roswell, GA (US); Jeffrey H. Mumm, Marietta, GA (US); Kam C. Lui, Kennesaw, GA (US)

(73) Assignee: Rheinische Kunststoffewerke GmbH, Worms (DE)

( * ) Notice: Subject to any disclaimer, the term of this patent is extended or adjusted under 35 U.S.C. 154(b) by 0 days.

(21) Appl. No.: 09/294,947

(22) Filed: Apr. 20, 1999

(65) Prior Publication Data

US 2002/0071944 A1 Jun. 13, 2002

Related U.S. Application Data

(60) Provisional application No. 60/082,514, filed on Apr. 21, 1998.

(51) Int. Cl.[7] ............................................. B32B 5/18
(52) U.S. Cl. ........................... 442/76; 442/79; 442/394; 442/398; 428/196; 428/198
(58) Field of Search ..................... 442/79, 76, 394, 442/398; 428/195, 196, 198

(56) References Cited

U.S. PATENT DOCUMENTS

| | | | |
|---|---|---|---|
| 4,124,563 A | 11/1978 | Onozuka et al. | 260/42.24 |
| 4,350,655 A | 9/1982 | Hoge | 264/145 |
| 4,472,328 A | 9/1984 | Sugimoto et al. | 264/41 |
| 4,613,463 A | 9/1986 | Sacks | 540/94 |
| 4,626,252 A | 12/1986 | Nishizawa et al. | 604/370 |
| 4,699,733 A | 10/1987 | Matsumura et al. | 282/521 |
| 4,704,328 A | 11/1987 | Imao et al. | 428/324 |
| 4,705,812 A | 11/1987 | Ito et al. | 521/92 |
| 4,705,813 A | 11/1987 | Ito et al. | 521/92 |
| 4,767,580 A | 8/1988 | Shingo et al. | 264/41 |
| 4,777,073 A | 10/1988 | Sheth | 428/155 |
| 4,791,144 A | 12/1988 | Nagou et al. | 521/90 |
| 4,793,956 A | 12/1988 | Nogiwa et al. | 264/41 |
| 4,794,128 A | 12/1988 | Kawaguchi et al. | 521/138 |
| 4,814,124 A | 3/1989 | Aoyama et al. | 264/41 |
| 4,822,350 A | 4/1989 | Ito et al. | 604/372 |
| 4,824,499 A | 4/1989 | Kagawa | 156/85 |
| 4,879,078 A | 11/1989 | Antoon, Jr. | 264/41 |
| 4,921,653 A | 5/1990 | Aoyama et al. | 264/41 |
| 4,923,703 A | 5/1990 | Antoon, Jr. | 426/118 |
| 4,929,303 A | 5/1990 | Sheth | 156/209 |
| 5,073,316 A | 12/1991 | Bizen et al. | 264/22 |
| 5,169,712 A | 12/1992 | Tapp | 428/315.5 |
| 5,173,356 A | 12/1992 | Eaton et al. | 428/219 |
| 5,176,953 A | 1/1993 | Jacoby et al. | 428/315.5 |
| 5,208,098 A | 5/1993 | Stover | 428/284 |
| 5,236,963 A | 8/1993 | Jacoby et al. | 521/92 |
| 5,422,172 A | 6/1995 | Wu | 428/230 |
| 5,445,862 A | 8/1995 | Kaneko et al. | 428/148 |
| 5,695,868 A | * 12/1997 | McCormack | 428/516 |

FOREIGN PATENT DOCUMENTS

| | | |
|---|---|---|
| EP | 0309073 | 3/1989 |
| WO | WO9424354 | 10/1994 |
| WO | WO9729909 | 12/1997 |
| WO | WO9805502 | 12/1998 |

OTHER PUBLICATIONS

DE 29805622 U1 Jul. 16, 1998 German (summary).*
DE 2737656 Mar. 1, 1979 German (summary).*

* cited by examiner

*Primary Examiner*—Terrel Morris
*Assistant Examiner*—Jenna-Leigh Befumo
(74) *Attorney, Agent, or Firm*—Ice Miller; Alexander D. Forman; Doreen J. Gridley

(57) ABSTRACT

This invention provides breathable composite materials with good liquid barrier properties comprising a laminate of a nonwoven web layer and a breathable film layer wherein breathability of the composite is provided by a plurality of point-like deformations of the film layer. In one embodiment, the composites also have a soft, cloth-like texture at at least one surface thereof. Also provided is a process for making such composites comprising applying a molten film-forming resin composition capable of developing breathability on deformation to a nonwoven web, cooling the molten composition to form a coated web having a web layer bonded to a film layer, and subjecting the coated web to heat and pressure at a plurality of points on a surface thereof wherein the heat, pressure and density of, and proportion of the composite surface occupied by, the deformations are effective to impart breathability to the film without loss of liquid barrier properties. In another embodiment of the process, web and cast film components are subjected to heat and pressure at a plurality of points to bond the film and the web and provide a plurality of point-like deformations of the film layer, thereby imparting breathability without loss of liquid barrier properties.

30 Claims, No Drawings

BREATHABLE COMPOSITE AND METHOD THEREFOR

This application claims the benefit of U.S. Provisional Application No. 60/082,514, filed Apr. 21, 1998.

FIELD OF THE INVENTION

This invention relates to breathable composites comprising film and fibrous nonwoven web layers and to manufacture of such composites.

BACKGROUND OF THE INVENTION

Breathable composites of thermoplastic films and fabrics are well known and are used in many applications, including construction wraps, disposable apparel and hygiene products. Composites of these types are generally characterized by breathability and liquid barrier properties that vary depending on porosity of the film layers and strength that varies with the nature of the fabric layers. For applications calling for low cost and light weight, the composites have been provided in the form of laminates of one or more layers of nonwoven fabric, or web, of thermoplastic filaments and one or more layers of breathable thermoplastic film. Examples of composites in that form and various utilities therefor are reported in commonly assigned U.S. Pat. No. 5,173,356, U.S. Pat. No. 5,208,098, U.S. Pat. No. 5,169,712, U.S. Pat. No. 5,176,953 and U.S. Pat. No. 5,236,963. An example of a strong, heavy-weight, durable composite is housewrap, formerly sold under the trademark Amowrap® by Amoco Foam Products Company, in the form of a laminate of a woven fabric and a permeable, perforated film.

Composites of porous films with uniform basis weight, continuous filament nonwoven fabrics and bonding thereof by means such as calendering, point embossing and needling are known from commonly assigned U.S. Pat. No. 5,173, 356. U.S. Pat. No. 5,169,712, also commonly assigned, discloses composites of various materials, including woven fabrics, nonwoven fabrics such as spunbonded and other continuous filament light weight nonwovens, melt blown fabrics and staple fiber nonwovens, with microporous films in which microporosity results from inclusion of low molecular weight polypropylene, an inorganic filler or a beta spherulite nucleating agent in a film-forming resin composition comprising polypropylene and ethylene-propylene copolymer. Various bonding techniques for the layers of the composites and utility thereof in various applications, such as disposable diaper components, housewrap, protective clothing, liners and automobile covers, are disclosed.

Composites of elastic films and nonwoven fabrics are disclosed in U.S. Pat. No. 5,422,172. The composites are prepared by extruding or coating an elastic, film-forming resin composition onto a nonwoven fabric and stretching the result uniformly across the laminate and throughout its depth. Stretching of the laminated film and fabric layers disrupts bonding of the filaments of the fabric such that on release of the stretching force the composite assumes an unstretched state with a multitude of filaments reportedly extending outwardly from a surface of the composite to form a lofty surface. Disclosed utilities for the composites are those in which elasticity, absorbency and softness are desirable; examples are said to include clothing articles, surgical gowns, sheets, dressings, hygienic products, baby diapers, baby training pants and catamenial pads. Typical laminates according to this patent include an impervious, elastic film layer. It is also noted that various degrees of air or vapor permeability may be achieved by providing mechanical microvoids to the films; however, there is no description or example of this concept.

U.S. Pat. Nos. 4,777,073 and 4,929,303 disclose laminates of fabrics and breathable films in which porosity of the film layer is achieved by stretching a particulate-filled film subjected to prior melt embossing so as to form thinner and thicker regions of the film. Stretching of the film results in regions of greater and lesser porosity.

Published International Application WO 97/29909 discloses a method for making microporous, cloth-like laminates of nonwoven fibrous webs and thermoplastic films. The laminates are said to have liquid barrier properties. As disclosed in this application, the laminates are made by laminating, by extrusion or adhesion, a nonwoven fibrous web and a microporous-formable thermoplastic film containing micropore-forming agents and then activating the pore formers by incremental stretching. A difficulty of this method is that the cloth-like surface of the laminate is sometimes achieved at the expense of a good bond between the film-forming and fibrous web layers. In addition, the stretching techniques used according to this publication are quite complex and rely on costly, highly specialized equipment.

There remains a need for improved, breathable laminates and methods for manufacture thereof. More specifically, some of the structures of the patents and publications discussed above suffer from harsh surface textures due to the inherent harshness of plastics from which low cost nonwoven fabrics are typically made. Thermal or adhesive bonding techniques used to laminate films and fabrics, such as bonding with smooth calender rolls, can result in composites with undesirable stiffness. Thermal bonding of microporous films to substrates can also disturb or destroy the films' porosity. It can also lead to formation of pinholes in the films, resulting in loss of strength, liquid barrier properties and other features. In other methods, breathability often is achieved at the expense of liquid barrier properties. Development of porosity in films by stretching after lamination of films and nonwoven webs, on the other hand, can lead to ineffective bonding between layers and nonuniform surfaces or surface textures. Such techniques also can be complicated and costly due to highly specialized equipment needs.

SUMMARY OF THE INVENTION

This invention provides breathable composites of breathable thermoplastic film and fibrous nonwoven web layers having good adhesion between the film and web layers, breathability and liquid barrier properties. The invention also provides a process for manufacture of breathable laminates of breathable film and fibrous nonwoven web layers having a desirable combination of properties.

In one embodiment, there is provided a breathable composite material having a hydrostatic head according to IST 80.4–92 of at least about 4 inches comprising at least one layer of breathable film comprising a thermoplastic resin composition laminated to at least one layer of a nonwoven web comprising filaments of a thermoplastic resin, wherein breathability of the film layer is provided by a plurality of discontinuous point-like deformations of the film layer. Preferred laminates according to this embodiment of the invention have a moisture vapor transmission rate according to ASTM E-96 Method E ("MVTR") of at least about 500 g/m$^2$ day.

In another embodiment, the invention provides a process for making breathable composites of films and nonwoven fibrous webs comprising applying to a nonwoven fibrous web comprising thermoplastic filaments a coating of molten, film-forming thermoplastic resin composition capable of developing breathability, cooling the molten resin to form a coated web and applying heat and pressure to the coated web at a plurality of points on a surface thereof to impart breathability to the coated web while substantially maintaining liquid barrier properties thereof.

Also provided is a process for making breathable composites of films and nonwoven fibrous webs comprising contacting a nonwoven fibrous web comprising thermoplastic filaments with a film comprising a thermoplastic resin composition capable of developing breathability and applying heat and pressure to the film in contact with the web at a plurality of points to bond the web and the film and develop breathability of the film at such points.

DETAILED DESCRIPTION OF THE INVENTION

The composites according to this invention are textile- or fabric-like structures in the form of laminates comprising nonwoven web and film layers having a desirable combination of breathability and liquid barrier properties. They have utility in a wide range of applications for both durable and disposable fabrics. Examples include disposable gowns and coveralls for hospital and industrial workers, components of diapers, hygiene products and disposable bedding such as sheets and pillow cases for hospital and other medical uses. The composites also can exhibit a soft, cloth-like texture at one or both surfaces thereof due to the nonwoven web, thereby promoting utility of the composites in applications for which film-nonwoven fabric composites have not heretofore found use due to their cost and aesthetics, including their harsh or stiff texture. An example of such applications is components of hygiene products such as backsheets for disposable diapers, and incontinence products. Furthermore, the laminates can be manufactured by a facile process well suited to in-line operations, with bonding of the film and nonwoven web layers and development of breathability of the film layer being achieved without sacrifices in breathability or barrier properties and without need for separate formation of a breathable film or exotic stretching equipment to develop breathability after lamination.

The composites comprise a nonwoven fabric-breathable film laminate. In one embodiment, the breathable film-nonwoven fibrous web laminates are breathable materials with hydrostatic head of at least about 4 inches, wherein breathability of the film layer is provided by a plurality of point-like deformations of the film layer.

As used herein, the expression "plurality of point-like deformations" means a number of small depressions or compressed areas that penetrate into the depth of the film layer but do not perforate or form holes in the layer. The term "point-like" is used to indicate that the deformations are essentially discrete from one another or are disposed essentially discontinuously over a surface of the layer. The term "point-like" is not, however, intended to imply limitations as to shape, size or pattern.

The deformations in the film layer in any given composite according to the invention can be of the same or different sizes and shapes and disposed regularly, irregularly or both over the film surface. Shape of the point-like deformations will depend on the means used to create the deformations but, from the standpoint of properties of the composite, is not critical. For example, the deformations can be, or approximate, circular, elliptical, semi-circular, triangular, rectangular, diamond, hexagonal, star-like, other parallelogram and polygonal shapes, as well as irregular shapes. The deformations can be disposed in a regular or irregular pattern or there can be no pattern. Size of the deformations and the proportion of the composite surface occupied by the deformations can affect the degree of breathability of the composite and, in a given composite, can be adjusted to provide varying levels of breathability. As a specific example, MVTRs in the range of about 1000 to about 1500 $g/m^2$ day are typical of composites having point-like deformations all of substantially the same size and shape occupying a total of about 16% of the composite surface and present in a regular pattern on such surface at a density of 196 points per square inch. Calculated area of such points, based on their density and percent of surface area covered by the same, is about 0.008 square inch per point. In general, point densities of about 100 to about 500 points per square inch, and preferably about 140 to about 400 points per square inch, disposed over about 8 to about 40%, and preferably about 10 to about 30%, of the surface provide MVTRs of at least about 500 $g/m^2/day$ and hydrostatic heads of at least about 4 inches of water. Combinations of point density and percent of surface area occupied by the deformations for achieving other ranges of MVTR can be determined by persons skilled in the art by experimentation guided by the teachings of this disclosure and the examples appearing herein. Adjusting the configuration of the deformations and/or proportion of the composite surface occupied by the deformations can be accomplished by any suitable means, including both equipment variations and process variations such as multiple passes of a composite through the equipment used to effect deformation of the composite surface.

Breathability of the laminates according to this embodiment of the invention is indicated by MVTR. Preferred composites have MVTRs of at least about 500 $g/m^2/day$. Hydrostatic head of such composites is at least 4 inches of water. MVTRs that are preferred range from about 1000 to about 8000 g/m 1 day and hydrostatic head is preferably at least about 7 inches. Given the teachings of the prior art with respect to pinhole formation due to point bonding of preformed porous films to fibrous webs and the need for lengthwise or widthwise stretching to develop porosity, it is unexpected to achieve such a combination of breathability and liquid barrier properties in the laminates according to this aspect of the invention. While lengthwise or widthwise stretching of the breathable laminates of the invention can be conducted to increase breathability, preferred composites are those in which breathability is provided by the plurality of deformations in the depth of the film layer without or with only insignificant, e.g., less than about 5%, lengthwise or widthwise stretching.

Another desirable feature of the composites is that the filaments of the nonwoven web can provide a desirable, cloth-like texture at at least one surface of the laminates. A soft, fuzzy texture is achieved despite thermal bonding of the film and nonwoven layers of the composites. Scanning electron microscope photographs of the composites show substantial adhesion of filaments of the nonwoven fabric to the film at an interface between the layers but also a substantial presence of unadhered segments of filaments. In combination, the fluid barrier properties, vapor permeability and clothlike texture of these composites make the same well suited for apparel and diaper applications.

The clothlike-textured laminates according to this embodiment of the invention are particularly well suited for diaper backsheet applications. Preferred composites for that use comprise a breathable film layer laminated to a nonwoven fabric layer and have MVTR of about 1000 to about 2500 g/m²/day, basis weights of about 10 to about 70 g/m² and hydrostatic head according to IST 80.4–92 of at least about 7 inches of water. Such composites have about 10 to about 30% of their surface area occupied by point-like deformations and about 100 to about 400 deformations per square inch. Thickness of the film layer of such composites for diaper backsheets preferably ranges from about 10 to about 55 microns because thinner films are difficult to produce without formation of holes, gaps and areas of nonuniform thickness while thicker films impart undesirable weight and stiffness. Thickness of the nonwoven fabric layer as present in such composites preferably ranges from about 70 to about 700 microns because thinner layers do not provide adequate fuzziness or softness to the composites while thicker layers add cost with little if any additional benefit and also may not be as easily bonded to the film layer as are thinner layers. Denier of the filaments of the nonwoven fabric layer of the composites for this application preferably range from about 1 to about 20 g/9000 m. In combination, the properties of such composites impart an ability to prevent passage of liquids but allow passage of water vapor for breathability and comfort under conditions of normal use. Furthermore, the soft, cloth-like surface of the composites has an appearance and texture much like that of conventional cloth diapers, thereby providing greater aesthetic appeal, including a less shiny surface than in conventional disposable diapers having a backsheet of monolithic plastic film.

In the invented laminates, preferred compositions of the film and nonwoven fabric layers comprise polyolefin resin compositions, such as polyethylenes, including low density polyethylene, high density polyethylene, linear low density polyethylene and so-called metallocene polyethylenes, polypropylene and copolymers of ethylene and propylene. Other suitable resin compositions for the film layer comprise thermoplastic resins capable of being provided in the form of film and of developing breathability, for example as a result of inclusion therein of finely divided particulates or other polymers or other additives that promote development of a breathability on deformation of films containing such additives. Examples of other suitable film-forming resins include ethylene vinyl acetate, methyl acrylate and ethylene acrylic acid copolymers.

Additives used in the film-forming resins to promote development of breathability include various finely divided inorganic and organic particulates, other polymeric resins and materials capable of promoting deviations in crystallite structure or properties within the film-forming resin. A preferred additive, owing to its cost, availability and effectiveness, is calcium carbonate. Other suitable particulates include talc, silica, clay, kaolin, alumina, aluminum hydroxide, magnesia, magnesium hydroxide, calcium sulfate, calcium sulfite, barium sulfate, aluminum silicate, calcium silicate, sodium silicate, potassium silicate, magnesium carbonate, calcium oxide, titanium dioxide, mica, glass flakes, zeolites, diatomaceous earth, perlite, vermiculite, glass microballoons, fly ash and glass beads. Polymeric resins that are suitable include phenolic resins and other resins that are incompatible with the film-forming resin in the sense that they are capable of retaining or substantially retaining their finely divided, particulate form through melt processing of the film-forming resin composition into film. Examples of crystallite-modifying agents include the gamma-crystalline form of a quinacridone colorant such as red quinacridone dye, the bisodium salt of ortho-phthalic acid, the aluminum salt of 6-quinizarin sulfonic acid, terephthalic acid and isophthalic acid. Generally, such particulates or additives have mean particle sizes of about 0.1 to about 10 microns and are present at levels of about 40 to about 200 parts by weight per hundred parts by weight of film-forming resin. These additives are generally described as promoting development of a pore structure or interconnected network of pores, with the pore size being small enough, and/or the pathway through the film provided by the pores being tortuous enough, that the films permit passage of gases but not liquids at temperatures and pressures encountered in normal use of the films. A wide range of resin compositions and additives for imparting breathability or porosity are known to those skilled in the plastics film art as seen from U.S. Pat. Nos. 4,350,655; 4,777,073; 4,929,303; 4,879,078; 4,923,703; 4,626,252; 4,794,128; 4,822,350; 4,124,563; 4,472,328;4,704,238; 5,073,316; 4,699,733; 4,705,812; 4,705,813; 4,814,124; 4,921,653; 4,793,956; 4,613,463; 4,767,580; 4,791,144; 5,445,862; and 4,824,499, which are incorporated herein by reference.

For the fibrous nonwoven web layer, any thermoplastic resin capable of being formed into filaments, such as by melt spinning, spunbonded techniques, melt blowing and centrifugal spinning, and of bonding to the film-forming resin is suitable. As noted above, the polyolefin resins are preferred. Other suitable resins include polyesters, rayon, acrylics, polyamides and thermoplastic elastomer resins such as styrene-ethylene-butylene copolymers and copolyester ethers. The composition of the film and fabric layers can be the same or different so long as adequate bonding of the layers at an interface therebetween can be achieved.

Particularly preferred laminates are those in which a film layer comprising a polyethylene resin composition is laminated to a nonwoven web layer in which the filaments comprise a polyethylene or polypropylene resin composition. Most preferably, the polyethylene resin composition of the film layer includes about 50 to about 150 parts by weight finely divided mineral particulates per hundred parts by weight polyethylene. Linear low density polyethylenes, ultra low density polyethylenes, so-called metallocene polyethylenes and blends thereof are most preferred resins for the film layer while calcium carbonate is most preferred as the mineral particulate. Mean particle size of the particulates generally ranges from about 0.1 to about 10 microns, with about 0.5 to about 3 microns being preferred.

Other features of the invented laminates will be determined largely based on end use requirements. Generally, basis weights of about 10 to about 300 g/m² are well suited for a wide range of applications, although weights outside that range are also contemplated depending on end use requirements. Basis weights that are preferred for disposable apparel and hygiene applications range from about 10 to about 80 g/m². Layer thicknesses within the laminates can also be varied over a wide range to tailor properties of the laminates to intended uses. Thicknesses of the nonwoven fabric layers range from about 70 to about 700 microns in order to achieve a fuzzy, cloth-like texture at the surface formed by the fabric layer with good bonding between the nonwoven web and film layers of the laminates. Filaments of the nonwoven webs having deniers on the order of about 1 to about 10 g/9000 m provide a fine, soft texture, while higher denier filaments, for example on the order of about 20 g/9000 m or greater, provide a coarse surface. Film layer thicknesses preferably range from about 10 to about 50 microns because greater thicknesses may lead to laminates having undesirable stiffness while thinner layers are more prone to formation of pinholes and, accordingly, poor liquid barrier properties.

The invented laminates can be provided in various configurations. Multi-layered configurations of the nonwoven fabric and breathable film layers, optionally with one or more layers of similar or dissimilar materials, are contemplated and can provide beneficial and interesting properties for various applications. For example, lamination or bonding of the film layer to scrims or extruded netting can provide additional strength and durability without sacrifices in breathability and liquid barrier properties. As another example, for applications calling for a breathable material having a cloth-like texture on both surfaces, a composite comprising at least one breathable film layer laminated between two outer surface layers of the nonwoven fabric can be provided. As a specific example of such a composite, a light weight laminate having an inner breathable film layer laminated to two outer surface layers of continuous filament nonwoven web, such as a polypropylene or polyethylene spunbonded or centrifugally spun web, provides a composite having a combination of breathability, liquid barrier properties, comfort, strength, light weight and low cost that is particularly well suited for disposable industrial protective garments.

The invented composites can be made by any suitable method for achieving effective bonding of the layers and localized deformation of the film layer effective to develop breathability, without fusion or other destruction of the surface of the fabric layer that forms an external surface of the laminate.

According to another aspect of the invention, there is provided a preferred method for making breathable film-fibrous nonwoven web laminates which can be conducted as an in-line process without pinhole formation detrimental to liquid barrier properties, thereby promoting process speed and high throughput. The process also avoids undesirable fusion of fabrics and promotes good surface texture of the resulting composites. It also is advantageous because it does not require forming the fabric and breathable film components of the laminates in separate operations.

The process according to this embodiment of the invention comprises applying to at least one surface of a fibrous nonwoven web a coating of a molten, film-forming thermoplastic resin composition capable of developing breathability, cooling the molten resin to form a coated web having a film layer bonded to a web layer and applying heat and pressure to the coated web at a plurality of points on at least one surface thereof, with the heat, pressure, proportion of the composite surface area occupied by the point-like deformations and density of the deformations being effective to impart breathability to the composite while maintaining liquid barrier properties. Coating of the nonwoven web with the film-forming resin composition provides a good bond between film and fabric layers. Breathability is provided as a result of deformation of the film surface at the points at which the heat and pressure are applied. This is accomplished without formation of pinholes in the film layer; accordingly, the resulting laminates have good liquid barrier properties.

Nonwoven fabrics suitable for use according to this embodiment of the invention include both continuous filament nonwovens, such as spunbonded and centrifugally spun fabrics, and fabrics comprising discontinuous or staple fibers, such as carded staple fiber webs, needlepunched nonwovens, hydroentangled webs and the like. Melt blown webs of continuous or discontinuous fibers also may be suitable although use of the resulting laminates in many applications is not practical due to the low strength of the webs. A preferred meltblown web is that described in U.S. Pat. No. 5,609,808. Preferred nonwoven fibrous webs are continuous filament nonwoven fabrics and particularly those having sufficient strength and integrity in both the machine and cross directions that they can be used in manufacture of the invented composites without prior thermal or adhesive bonding. An example of such a web is the continuous filament nonwoven fabric identified as RFX® Fabric available from Amoco Fabrics and Fibers Company. Lightly calendered or point bonded spunbonded webs, RFX® Fabrics and other centrifugally spun continuous filament webs also are good choices as are needlepunched staple fiber webs and thermally bonded, carded staple fiber webs.

The filaments of the nonwoven webs can comprise any suitable material capable of bonding with the film-forming resin on coating therewith. Although the fabrics can be composed of or contain natural fibers, preferred nonwovens are those comprising synthetic filaments or fibers of one or more thermoplastic resin compositions. Polyolefin filaments and fibers, and particularly those comprising polypropylene, a polyethylene or a copolymer of ethylene and propylene are particularly preferred for many diverse applications due to their ease of processing, low cost, hydrophobicity, strength and resistance to mold, mildew and aqueous stains. Other suitable thermoplastic resins are those capable of being spun or otherwise processed into fibers; examples include polyesters, nylons, acrylic polymers and thermoplastic elastomers such as styrene-butadiene copolymers, styrene-ethylene-butylene copolymers and copolyester-ethers.

The nonwoven fabrics or the filaments or fibers thereof can contain or have applied thereto various additives and modifiers. Such materials include pigments and colorants, antioxidants, stabilizers, antimicrobial agents, stain resisting additives, flame retardants and the like. These materials and their use are well known and suitable levels for particular applications can be determined by persons skilled in the art or arts related to such applications.

Other characteristics and features of the nonwoven fabrics used in the invented process can vary widely. Conceptually, there is no limit on the basis weights or filament deniers of the fabrics although practical considerations such as equipment size and configuration, process economics and end use requirements may dictate requirements or preferences in one or more respects. Generally, basis weights of about 15 to about 80 $g/m^2$ and filament deniers of about 1 to about 15 g/9000 m are well suited for hygiene and disposable apparel applications. Heavier fabrics, such as those with basis weights of about 40 to about 150 $g/m^2$, and/or those with coarser filaments, such as those with deniers of about 5 to about 25 g/9000 m are preferred for applications having more demanding requirements in terms of strength and durability, such as roofing underlayments.

The film-forming resin composition that is applied in molten form to the nonwoven fabric according to the invented process comprises at least one thermoplastic resin that can be melted and formed into film and can bond to the fabric. The film-forming composition also must be capable of developing breathability on deformation thereof. Various film-forming thermoplastic resins are well known; examples useful in the invented process include polyolefins such as polypropylene, polyethylenes and copolymers of ethylene and propylene; ethylene vinyl acetate copolymers, ethylene methyl acrylate copolymers and ethylene acrylic acid copolymers. Preferred resins are polypropylene, high density polyethylene, linear low density polyethylenes, metallocene polyethylenes and so-called ultra low density polyethylenes.

The film-forming resin composition also comprises one or more additives that promote or enhance development of breathability in the film upon deformation. A wide range of such additives is known and includes inorganic and organic particulates, other polymeric resins, and agents capable of promoting crystallite modifications that can be exploited to achieve breathability. Further description and examples of such materials are provided above.

These breathability-promoting additives are used in amounts effective to promote development of breathability in the film-forming resin when coated onto the fibrous web and subjected to heat and pressure. Generally, about 40 to about 200 parts by weight of the additive is used per hundred parts by weight resin, with about 80 to about 120 parts per hundred parts resin being preferred to promote desirable levels of breathability without complicating film formation due to high levels of additives. Mean particle size of the additives is generally about 0.1 to about 10 microns, with about 0.5 to about 5 microns being preferred, again to facilitate development of breathability without complicating film extrusion.

Various resin compositions and additives for forming breathable films are disclosed in the patents listed and incorporated by reference hereinabove. The film-forming resin composition can also contain various additives, fillers and modifiers. Examples include pigments and colorants, heat, light and oxidation stabilizers and process aids. These materials and their use, including formulation and compounding thereof with appropriate resins and amounts of specific additive compositions and combinations thereof effective for various purposes, are well known to persons skilled in the film manufacturing and converting arts.

According to the process of this embodiment of the invention, the film-forming resin composition, including breathability-promoting additive, is coated onto the fibrous web with the film-forming resin in a molten state, the resin is cooled to solidify the same and form a coated web, and the coated web is subjected to heat and pressure at a series of points on the surface thereof to provide a plurality of point-like deformations in the film and develop breathability. Preferably, heat and pressure are applied using an embossing roll engraved to provide a plurality of points. As in the previous description of the invented composites, the term "point", as used in describing the invented method, refers to a localized or discrete area but is not otherwise to be considered limited as to size or shape.

Coating of the web with the film-forming resin composition capable of developing breathability can be conducted by any suitable means for applying a coating of molten resin continuously over a surface of the web. It is to be understood that the coating is applied continuously over the surface of the web in the sense that there are not gaps, interruptions or discontinuities in the coating that leave portions of the surface of the web uncoated. It is preferred that the coating be applied to the web so that the thickness of the coating is substantially uniform. Most conveniently, application of the coating to the web is accomplished by extrusion coating a surface of the web with the composition with the film-forming resin in a molten state. Extrusion coating techniques are well known and generally involve melting and working the resin composition as it passes through an extruder barrel due to rotation of a screw located within the barrel and issuing the molten composition from a die. Extrusion conditions vary depending on choice of film-forming composition and melt viscosity thereof, but generally include temperatures of about 50 to about 170° C., and preferably about 100 to about 150° C., above the melting or softening temperature of the thermoplastic resin included in the composition. For example, when using filled film-grade polyethylene resins melting at about 125° C., typical extrusion temperatures range from about 180 to about 280° C.

The molten film-forming resin composition is extrusion coated onto a surface of the nonwoven web. Preferably, the molten resin is coated onto the web at or slightly upstream from a nip formed by rotating rolls. The rolls exert a force on the coated web as it passes through the nip, thereby promoting bonding of the extruded coating to the filaments of the web. Nip forces of about 10 to about 120 pli preferably are employed to achieve good bonding of the coating to the web at the interface between such layers without damage to the filaments of the web at the web surface opposing such interface. More preferably, nip force ranges from about 30 to about 90 pli. Roll temperatures can be varied as needed to cool the molten resin and solidify the same while also preventing heat transfer from the molten resin to the web to such an extent as to fuse or otherwise damage the filaments of the web at the surface opposite the web-coating interface. Line speeds will vary depending on equipment configuration and capabilities and process economics. Generally, the coating process can be operated at line speeds of about 20 to about 700 feet/min. with good results.

The resulting coated fabric is then subjected to heat and pressure at a plurality of points on a surface thereof for the purpose of developing breathability of the film layer. Application of heat and pressure to the coated web at a number of points on the surface thereof serves to deform the film layer at and near the points. On deformation of the film layer, the breathability-promoting additive promotes development of breathability of the film. Application of heat and pressure, together with the density and area of the points, are controlled so that adequate breathability of the film layer, and in turn the composite, is achieved without sacrificing liquid barrier properties due to formation of holes in the film. Heat and pressure can be applied to the coated fabric at either or both of the web surface and the coated surface with good results. Usually, application of heat and pressure to the web surface tends to promote cloth-like texture of the web surface of the resulting laminate to a greater extent than application to the film surface. Other things being equal, it also may provide composites of greater breathability.

Generally, temperatures and pressures employed during the application of heat and pressure are great enough to cause deformation in the depth of the film layer without making holes in the same and without fusion of filaments of the nonwoven web layer at or near the points into impermeable masses. As will be appreciated, temperatures and pressures will vary depending on melting points of the resins of the film and nonwoven web layers, thicknesses of the layers and degree of breathability desired in the laminated structure. Preferably, temperatures of about 100° C. below the melting point of the film-forming resin up to the melting point are employed to achieve suitable deformation without pinhole formation. More preferably, temperatures about 20 to about 50° C. below the melting point are used. When the film forming resin composition comprises a blend of resins having different melting temperatures, temperatures used in the deformation step are typically based on the melting point of the primary resin of the composition, e.g., that constituting the greatest weight fraction of the film-forming composition. For in-line processes in which coating of the web with the film-forming composition and deformation are conducted continuously, preferred deformation temperatures range from about 70 to about 220° C. below the extrusion temperature of the film-forming resin composition. Nip forces preferably range from about 200 to about 2000 pli.

The number of points per unit area and proportion of the composite surface area occupied by the deformations also affect the degree of breathability. Laminates with points occupying from about 8 to about 40% of their surface area and with about 100 to about 500 points per square inch have breathabilities, as indicated by MVTRs of at least about 500 g/m$^2$/day, well suited for a wide range of applications.

A preferred method of applying heat and pressure at a plurality of points on the surface of the coated web is to pass the same through an embossing roll system in which at least one roll has been engraved or otherwise machined or treated to impart a plurality of raised points or areas to the surface thereof. The raised points or areas can, though need not, be disposed in a repeating pattern on the surface of the roll. The points can be of any desired shape. Examples are described above. For application of heat and pressure to laminates in which the nonwoven web layer is composed of polyethylene or polypropylene filaments and the web is coated with a film layer comprising a polyethylene as the thermoplastic resin, temperatures ranging from about 140 to about 220° F., nip forces of about 300 to about 1500 pli, and embossing patterns with points occupying about 8 to about 40% of the laminate's surface area with about 100 to about 500 points per square inch can be used with good results. Multiple passes through an embossing roll system or passage through two or more embossing systems arranged in series can be utilized to vary the degree of breathability of the laminates. Temperatures of the embossing rolls also can be adjusted to control breathability, with higher temperatures generally providing higher MVTRs.

In a preferred embodiment of the invention, the above described method is utilized to prepare breathable laminates of the type described hereinabove having hydrostatic head of at least about 4 inches of water and wherein breathability is imparted by a plurality of point-like deformations of the film layer. More preferably, a film-forming polyolefin resin composition comprising at least one finely divided inorganic particulate material, most preferably calcium carbonate, is extrusion coated at a thickness of about 15 to about 60 microns onto a nonwoven web of substantially continuous polyolefin filaments, the film-forming resin composition is cooled to form a coated web having a film layer bonded to the web, and the coated web is point embossed at a temperature of about 140 to about 230° F. and nip force of about 700 to about 1500 pli such that about 8 to about 40% of the surface area of the coated web is occupied by embossed points and the points are present on a surface of the laminate at a density of about 100 to about 500 points per square inch.

According to another aspect of the invention, there is provided a method for making breathable film-fibrous nonwoven web laminates comprising contacting a nonwoven fibrous web comprising thermoplastic filaments with a film comprising a thermoplastic resin composition capable of developing breathability and applying heat and pressure to the film in contact with the web at a plurality of points to bond the web and the film at a plurality of points and form a plurality of point-like deformations of the film. Compositions and configurations of the film and web components used in the method according to this aspect of the invention are described above. The thermoplastic resin compositions capable of developing breathability typically are extruded to form film at temperatures of about 50–120° C. above the melting point of the thermoplastic resin of which the film is composed. Preferred temperatures for deforming such films to impart breathability and achieve bonding of the film to the web layer range from about 30° C. below to about 40° C. above the melting point of the film-forming resin or, in the case of film-forming resin blends, the melting point of the primary resin component. More preferably, temperatures from about 20° C. below to about 30° C. above such melting point are used. For processes in which a free-standing film is prepared and then fed directly to equipment for bonding with the web layer and deformation, particularly preferred temperatures for the bonding and deformation step range from about 40 to about 160° C. below the film extrusion temperature. In other respects, the process according to this aspect of the invention is carried out in a manner similar to that described above with respect to subjecting a coated web to heat and pressure to provide a plurality of point-like deformations on the surface of the composite.

The invention is described further in connection with the following examples, it being understood that the same are for purposes of illustration and not limitation. In the examples, the following test methods were used:

Moisture Vapor Transmission Rate ("MVTR"): ASTM E-96 Method E;

Water Resistance Hydrostatic Pressure Test ("HH"): IST 80.4–92;

Melt Index ("MI"): ASTM D1238 Condition E (190° C., 2.16 kg weight);

Tensile Strength: ASTM D5034–95.

The Following Materials Were Used:

Polyethylene Concentrate: A masterbatch, identified as LCC-708X from A. Schulman, Inc., Akron, Ohio., containing of a blend of two linear low density polyethylene resins and 68.3 weight % calcium carbonate powder having a median particle size of 0.7 micron, identified as Omyacarb UFT. The masterbatch had a MI of 3.5 g/10 minutes and contained a 2.0 g/10 minutes MI, 0.918 g/cm$^3$ density linear low density polyethylene and a 20.0 g/10 minutes MI, 0.924 g/cm$^3$ density linear low density polyethylene. MI of the polyethylenes, before addition of calcium carbonate, was 8 g/10 minutes.

LLDPE: Linear low density polyethylene having MI of 1.0 g/10 minutes and density of 0.935 g/cm$^3$ identified as Dowlex® 2038 from The Dow Chemical Company.

ULDPE: A polyolefin plastomer resin having MI of 1.0 g/10 minutes and density of 0.87 g/cm$^3$ identified as Affinity EG 8100 from The Dow Chemical Company.

Fabric A was a light weight, point embossed, nonwoven web of substantially continuous polypropylene filaments having average basis weight of 20.0 g/m$^2$ (0.59 osy), machine direction elongation of 97% and cross direction elongation of 188%, with a 16% bonded area, 30 points per square cm (196 points per square inch) diamond bonding pattern, identified as RFX® Fabric made by Amoco Fabrics and Fibers Company.

Fabric B was a 32 g/m$^2$ (0.94 osy) average basis weight, polyethylene continuous filament nonwoven web point embossed in the same manner as Fabric A having machine direction elongation of 118% and cross direction elongation of 252%, identified as RFX® Fabric made by Amoco Fabrics and Fibers Company.

Fabric C was a polyethylene RFX® Fabric that was the same as Fabric B except it had average basis weight of 17 g/m$^2$ (0.5 osy).

Fabric D was a polypropylene RFX® Fabric that was the same as Fabric A except it had average basis weight of 22 g/m$^2$ (0.66 osy), machine direction elongation of 62% and cross direction elongation of 166%.

Each of Fabrics A, B, C and D was made substantially according to the procedure of commonly assigned U.S. Pat. No. 5,173,356.

Fabric E was a web of thermally bonded, carded polypropylene staple fiber having average basis weight of 20 g/m$^2$ (0.59 osy), machine direction elongation of 44% and cross direction elongation of 78% manufactured by Amoco Fabrics Division, Niederlassung der Amoco Deutschland GmbH.

EXAMPLE 1

A resin mixture was prepared by compounding 70 parts by weight Polyethylene Concentrate, 10 parts by weight LLDPE and 20 parts by weight ULDPE in a 34 mm co-rotating, intermeshing twin screw extruder at 200° C. at a rate of 50 lbs/hr. Extrudate strands were water quenched and cut into pellets approximately 3 mm long by 2 mm in diameter. The resin pellets were tumble-dried for 4 hours at 1–5 mm Hg vacuum at 60° C. MI of the compounded resin was 1.1 g/10 min.

The compounded resin was extruded as a 20 $\mu$ (0.8 mil) thick, 13 cm (5.25 inch) wide film onto Fabric A passing from an unwind roll to a chill roll-nip roll combination at a speed of 24 m/min (80 ft/min). The extrusion was conducted using a 2-inch diameter, single screw extruder with a slot die. The resin temperature in the extruder barrel was 246° C. The resin was extruded onto the fabric immediately upstream of the nip between the chill and nip rolls and the resulting, coated fabric was passed through the nip between the rolls and to a take-up roll. The chill roll had a smooth steel surface and was maintained at about 30° C. with circulating water. The nip roll was a hard rubber roll. Force at the nip was about 9 kg/cm (50 pounds per lineal inch ("pli")). Average basis weight of the resulting laminate was about 80 g/m$^2$ (2.3 osy). It had average MVTR of 52 g/m$^2$/day and hydrostatic head greater than 50 inches of water.

A coated web prepared as described above was point embossed by passage between a smooth steel roll and a second steel roll engraved to provide 196 bond points per square inch and a bonded area of 16% with the bonding points extending to a height of 0.033 inch from the base of the roll. The points were in the shape of elongated diamonds with their longer dimensions oriented in the machine direction, i.e., axially relative to the roll surface, and their shorter dimensions in the cross direction, i.e., parallel to the axis of the roll. The rolls were heated at 210° F., pressure at the nip between the rolls was 1427 pli and line speed was 15 ft/min. The coated web was passed through the embossing roll pair with the web surface in contact with the engraved roll and the coating surface in contact with the smooth roll.

The resulting laminate had average MVTR of 1361 g/m$^2$/day, HH of 7.5 inches water and weight of 64 g/m$^2$ (1.9 osy). It is believed that basis weight of this sample was less than that of the coated web described above due to basis weight variations among different samples of Fabric A. Texture of the laminate at the surface formed by the fabric was soft and cloth-like.

EXAMPLE 2

A coated web was prepared substantially as in Example 1 except that Fabric B was used, thickness of the film layer extruded onto the web was 0.85 mil, width of the sample was 4.3 inches, melt temperature during extrusion was 246° C. and take up speed was 62 ft/min. The resulting coated web had average MVTR of 44 g/m$^2$/day, hydrostatic head of 30.5 inches of water and weight of 73 g/m$^2$ (2.15 osy). A sample of the coated web was point embossed as in Example 1 except the force at the nip between the engraved and smooth rolls was increased to 1600 pli. The resulting laminate had average MVTR of 940 g/m$^2$/day, HH of 7.2 inches water and weight of 75 g/m$^2$ (2.2 osy). Texture of the web surface of the laminate was soft and cloth-like.

EXAMPLE 3

Compounded resin as in Example 1 was extruded into film having a thickness of about 0.5–0.7 mil and width of 16 inches using a 2.5 inch diameter extruder with a 16 inch flat film die with the die gap set at 0.01 inch. The extruder was operated at 380° F. melt temperature and 4.3 rpm gear pump speed. The film was extruded onto a quench roll heated at 100° F. operated at a speed of 40 ft/min and passed to a take up roll also operated at 40 ft/min. The resulting film had average MVTR of 48 g/m$^2$/day, indicating that it was substantially impervious. Average basis weight was 25 g/m$^2$ (0.75 osy). The film was not tested for HH due to its substantially impervious nature.

A sample of the film was laminated to Fabric A by point embossing substantially as in Example 1 except that temperatures of the smooth and engraved rolls were 235° F., force at the nip between the rolls was 555 pli and line speed was 160 ft/min. The resulting laminate had average MVTR of 1066 g/m$^2$/day, HH of 9.7 inches water and weight of 47 g/m$^2$ (1.4 osy). Texture of the laminate at the surface formed by the fabric was soft and cloth-like.

EXAMPLE 4

A sample of the film from Example 3 was laminated to Fabric C by point embossing substantially as in Example 1 except that roll temperatures were 210° F., line speed was 25 ft/min and nip force was 555 pli. The resulting laminate had average MVTR of 1319 g/m$^2$/day, HH of 8.4 inches water and weight of 39 g/m$^2$ (1.2 osy). Texture of the laminate at the surface formed by the fabric was soft and cloth-like.

The above procedure was repeated except that the point embossing was conducted with the coating surface contacting the engraved roll and the web surface contacting the smooth roll. Average MVTR of the result was 789 g/m$^2$/day and average HH was 8.0 inches of water.

As seen from the foregoing, MVTRs of the coated webs in Examples 1 and 2, before deformation by point embossing, and of the unbonded film in Example 3, were in the range of 40–50 g/m$^2$/day, indicating that they were substantially impermeable. However, deformation of the film layers in all of the examples resulted in MVTRs in excess of 500 g/m$^2$/day, with most of the examples being about 1000–1500 g/m$^2$/day, thus indicating good breathability. Further, it can be seen that such MVTRs were achieved with good liquid holdout, as indicated by HH values above 7 inches of water. This combination of properties in a point embossed breathable film—nonwoven web laminate was surprising in view of prior art teachings that point bonding of porous films to nonwoven webs tends to cause formation of pinholes in the films and, as a result, poor liquid barrier properties. In view of prior art teachings regarding the need for stretching or deformation of films in their lengthwise or widthwise dimension to develop breathability, attainment of the MVTRs of the laminates in Examples 1–4 by application of heat and pressure to form a plurality of point-like deformations was also unexpected.

EXAMPLE 5

Fabric D was extrusion coated with a 1 mil film as in Example 1. Samples of the coated fabric were point embossed at 550 pli using equipment as in Example 1 but with variations in roll temperatures and number of passes through the embossing roll system. Conditions and average MVTRs and HHs of the resulting laminates are shown below.

| SAMPLE | CONDITIONS | MVTR(g/m$^2$/day) | HH (inches of water) |
|---|---|---|---|
| A | 1 pass/160° F. | 152 | 17.3 |
| B | 4 passes/160° F. | 756 | 8.0 |
| C | 1 pass/180° F. | 177 | 9.0 |
| D | 4 passes/180° F. | 1141 | 8.0 |
| E | 1 pass/210° F. | 800 | 8.7 |

As seen from the table, multiple passes through the embossing rolls and/or variations in embossing temperatures can be utilized to achieve varying levels of breathability and liquid barrier properties. It can also be seen that comparable levels of MVTR and HH can be achieved at different temperatures by varying the number of passes.

EXAMPLE 6

Fabric D was extrusion coated with a 1 mil film as in Example 1. Samples of the coated fabric were point embossed at 550 pli in the same manner as Example 5 except that the embossing roll was an engraved roll with a continuous, inverted wire weave pattern having 412 bond points per square inch with the points extending to a height of 0.020 inch from the base of the roll. The points occupied about 37% of the area of the composite. Samples were embossed at various temperatures, as shown below. Average MVTRs and HHs of the resulting laminates are also shown below.

| SAMPLE | TEMPERATURE | MVTR(g/m$^2$/day) | HH (inches of water) |
|---|---|---|---|
| F | 160° F. | 557 | 10.2 |
| G | 180° F. | 1358 | 10.2 |
| H | 210° F. | 2682 | 8.8 |

As seen from the table, variations in embossing temperature can be utilized to achieve varying levels of breathability and liquid barrier properties. Texture of the web surface of the resulting composites was soft and cloth-like though less so than in the previous examples due to the greater proportion of the area of the composite occupied by the point-like deformations.

EXAMPLE 7

A sample of Fabric E was extrusion coated with a 1 mil film as in Example 1. Samples of the coated fabric were point embossed at 833 pli using equipment as in Example 1 but with variations in roll temperatures and number of passes through the embossing roll system. Conditions and average MVTRs and HHs of the resulting laminates are shown in the following table.

| SAMPLE | CONDITIONS | MVTR(g/m$^2$/day) | HH (inches of water) |
|---|---|---|---|
| I | 1 pass/160° F. | 208 | 13.7 |
| J | 4 passes/160° F. | 1150 | 9.3 |
| K | 1 pass/180° F. | 286 | 18.0 |
| L | 4 passes/180° F. | 2028 | 10.8 |
| M | 1 pass/210° F. | 1267 | 9.5 |

This example demonstrates that composites with useful combinations of breathability and liquid barrier properties can be obtained using a carded staple fiber web as the fabric or web component of the laminate. It can also be seen from the table that multiple passes through the embossing rolls and variations in embossing temperatures can be utilized to achieve varying levels of breathability and liquid barrier properties, and that comparable levels of MVTR and HH can be achieved at different temperatures by varying the number of passes.

EXAMPLE 8

Fabric E was extrusion coated with a 1 mil film as in Example 1. Samples of the coated web were point embossed at 833 pli in the same manner as in Example 6. Roll temperatures and average MVTRs and HHs of the resulting composites are shown below.

| SAMPLE | TEMPERATURE | MVTR(g/m$^2$/day) | HH (inches of water) |
|---|---|---|---|
| N | 160° F. | 614 | 12.5 |
| O | 180° F. | 1475 | 10.0 |
| P | 210° F. | 4823 | 6.7 |

As seen from the table, variations in embossing temperatures resulted in varying levels of breathability and liquid barrier properties.

EXAMPLE 9

Fabric E was extrusion coated with a 1 mil film as in Example 1. Samples of the coated fabric were point embossed at 550 pli as in Example 5 except that the engraved roll had 388 bond points per square inch and 22% of its surface area occupied by the points. The points were in the shape of elongated diamonds with their longer dimension oriented in the cross direction. Height of the bonding points above the base of the roll was about 0.030 inch. Temperature was varied from run to run and is shown below together with average MVTRs and HHs of the resulting laminates.

| SAMPLE | TEMPERATURE | MVTR(g/m$^2$/day) | HH (inches of water) |
|---|---|---|---|
| Q | 160° F. | 67 | 27.7 |
| R | 180° F. | 148 | 12.2 |
| S | 210° F. | 657 | 10.5 |

Again, variations in embossing temperature resulted in changes in breathability and liquid barrier properties of the laminates.

Comparative Example 1

A sample of the film prepared in Example 3 was stretched in a manner similar to that described in U.S. Pat. No. 4,116,892. The extent of the stretching was such that the ratio of stretched length of the film to unstretched length was 1.25:1 in the machine direction and 1.12:1 in the cross direction. The stretched film had an average MVTR of 1283 g/m$^2$/day; however, results for individual samples ranged from a low of 288 g/m$^2$/day to a high of 2791 g/m$^2$/day, thus indicating that the results of the stretching were highly variable. Similarly, hydrostatic head of the stretched film showed considerable variability, ranging from 7.5 to 13 inches of water and averaging 11.3 inches of water. Average weight of the stretched film was 19 gsm (0.55 osy).

Comparative Example 2

The laminate from Example 4 was stretched approximately 12% in each of the machine and cross directions following substantially the procedure of Comparative Example 1. Numerous pinholes were observed at the embossed areas of the resulting laminate. It was not tested for MVTR or HH because the presence of the pinholes indicated that HH would not be acceptable.

Comparative Example 3

A sample of the film prepared in Example 3 and Fabric A were passed through the point embossing rolls as in Example 3 with the rolls heated at 220° F. The film and fabric layers of the resulting structure separated when gently stretched, showing poor adhesion between the layers.

We claim:

1. A breathable composite having hydrostatic head according to IST 80.4–92 of at least about 4 inches comprising a laminate of at least one fibrous, nonwoven web layer and at least one thermoplastic film layer, the laminate being stretched no more than about 5% in a lengthwise and widthwise direction, and wherein the film layer comprises at least one thermoplastic resin, a finely divided particulate material capable of promoting breathability, and a plurality of point-like deformations which provide breathability of the composite, wherein the breathable composite has a breathability of at least about 500 g/m²/day.

2. The composite of claim 1 having a MVTR of at least about 500 g/m²/day, where the laminate can be stretched to less than about 5% lengthwise or widthwise stretching.

3. The composite of claim 2 wherein the fibrous nonwoven web layer comprises filaments comprising at least one polyolefin resin.

4. The composite of claim 2 wherein the thermoplastic film layer comprises at least one polyolefin resin.

5. The composite of claim 2 wherein the thermoplastic film layer comprises at least one polyolefin resin and the nonwoven web layer comprises filaments comprising at least one polyolefin resin.

6. The composite of claim 5 wherein the nonwoven web layer has substantial segments of filaments unadhered to the film layer whereby a cloth texture suitable for diaper and apparel uses is provided on at least one surface of the composite.

7. The composite of claim 5 having a hydrostatic head of at least about 7 inches.

8. The composite of claim 7 wherein the polyolefin resin of the thermoplastic film layer comprises at least one polyethylene resin.

9. The composite of claim 8 wherein the polyolefin resin of the filaments comprises at least one polyethylene resin.

10. The composite of claim 8 wherein the polyolefin resin of the filaments comprises at least one polypropylene resin.

11. The composite of claim 7 wherein the polyolefin resin of the thermoplastic, breathable film layer comprises at least one polypropylene resin.

12. The composite of claim 11 wherein the polyolefin resin of the filaments comprises at least one polyethylene resin.

13. The composite of claim 11 wherein the polyolefin resin of the filaments comprises at least one polypropylene resin.

14. A breathable composite comprising a laminate comprising at least one film layer and at least one nonwoven web layer, the laminate being no more than insignificantly stretched in a lengthwise and widthwise direction, and wherein the nonwoven web layer comprises filaments of at least one polyolefin resin, and the film layer comprises a polyolefin resin, a finely divided particulate material capable of promoting breathability, and a plurality of embossed, point-like deformations, such deformations providing breathability of the composite by occupying about 8 to about 40% of the area of a surface of the composite and being present on such surface at a density of about 100 to 500 points per square inch.

15. The composite of claim 14 wherein the polyolefin resin of the film layer comprises at least one polyethylene resin.

16. The composite of claim 15 wherein the nonwoven web layer comprises a web of substantially continuous filaments.

17. The composite of claim 16 wherein the filaments comprise at least one polypropylene resin.

18. The composite of claim 17 wherein filaments of the web of substantially continuous filaments provide a cloth texture to said nonwoven web layer on at least one surface of the composite.

19. The composite of claim 16 wherein the filaments comprise at least one polyethylene resin.

20. The composite of claim 19 wherein filaments of the web of substantially continuous filaments provide a cloth texture to said nonwoven web layer on at least one surface of the composite.

21. The composite of claim 15 wherein the nonwoven web layer comprises a web of staple fibers.

22. The composite of claim 21 wherein the staple fibers comprise at least one polypropylene resin.

23. The composite of claim 22 wherein staple fibers of the web of staple fibers provide a cloth texture to said nonwoven web layer on at least one surface of the composite.

24. The composite of claim 21 wherein the staple fibers comprise at least one polyethylene resin.

25. The composite of claim 23 wherein staple fibers of the web of staple fibers provide a cloth texture to said nonwoven web layer on at least one surface of the composite.

26. Them composite of claim 14 wherein the polyolefin resin of the film layer comprises at least one polypropylene resin.

27. The composite of claim 14 wherein the nonwoven web layer comprises a web of substantially continuous filaments comprising at least one polypropylene resin.

28. The composite of claim 14 wherein the nonwoven web layer comprises staple fibers comprising at least one polypropylene resin.

29. The composite of claim 14 wherein the nonwoven web layer comprises a web of substantially continuous filaments comprising at least one polyethylene resin.

30. The composite of claim 14 wherein the nonwoven web layer comprises staple fibers comprising at least one polyethylene resin.

* * * * *